US00PP34908P3

(12) United States Plant Patent
Schoone

(10) Patent No.: US PP34,908 P3
(45) Date of Patent: Jan. 10, 2023

(54) ***PHALAENOPSIS* PLANT NAMED 'DIAMOND SKY'**

(50) Latin Name: *Phalaenopsis hybrida*
Varietal Denomination: Diamond Sky

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/666,154

(22) Filed: Feb. 7, 2022

(65) Prior Publication Data

US 2022/0256756 P1 Aug. 11, 2022

Related U.S. Application Data

(60) Provisional application No. 63/147,984, filed on Feb. 10, 2021.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./263.1, 311
See application file for complete search history.

(56) References Cited

PUBLICATIONS

Fox News: New Bloom: Never-Before Seen Orchid to Debut at Kew Festival. https://www.nbcnews.com/pop-culture/pop-culture-news/new-bloom-never-before-seen-orchid-debut-kew-festival-n24011. 2 pgs. (Year: 2014).*
Art.com. New Orchid *Phalaenopsis* 'Diamond Sky' on display at the Kew Orchid Festival. https://www.art.com/products/p36998762183-sa-i9660965/new-orchid-phalaenopsis-diamond-sky-on-display-at-the-kew-orchid-festival-kew-gardens-london.htm. 2 pgs. (Year: 2022).*
Bridgeman images. New Orchid *Phalaenopsis* 'Diamond Sky' on display at the Kew Orchid Festival. https://www.bridgemanimages.com/en-US/noartistknown/new-orchid-phalaenopsis-diamond-sky-on-display-at-the-kew-orchid-festival-kew-gardens-london-photo/colour-photograph/asset/1065002. 2pgs. (Year: 2022).*

* cited by examiner

*Primary Examiner* — Karen M Redden
(74) *Attorney, Agent, or Firm* — C. Anne Whealy

(57) ABSTRACT

A new and distinct cultivar of *Phalaenopsis* plant named 'Diamond Sky', characterized by its upright plant habit; moderately vigorous growth habit; strong flowering stems; strong and slightly elongated leaves; freely flowering habit with typically two inflorescences per plant, each inflorescence with numerous flowers; white-colored flowers with yellow-colored labellum and a small number purple-colored spots surrounding the column; and good postproduction longevity.

2 Drawing Sheets

Figure 1:
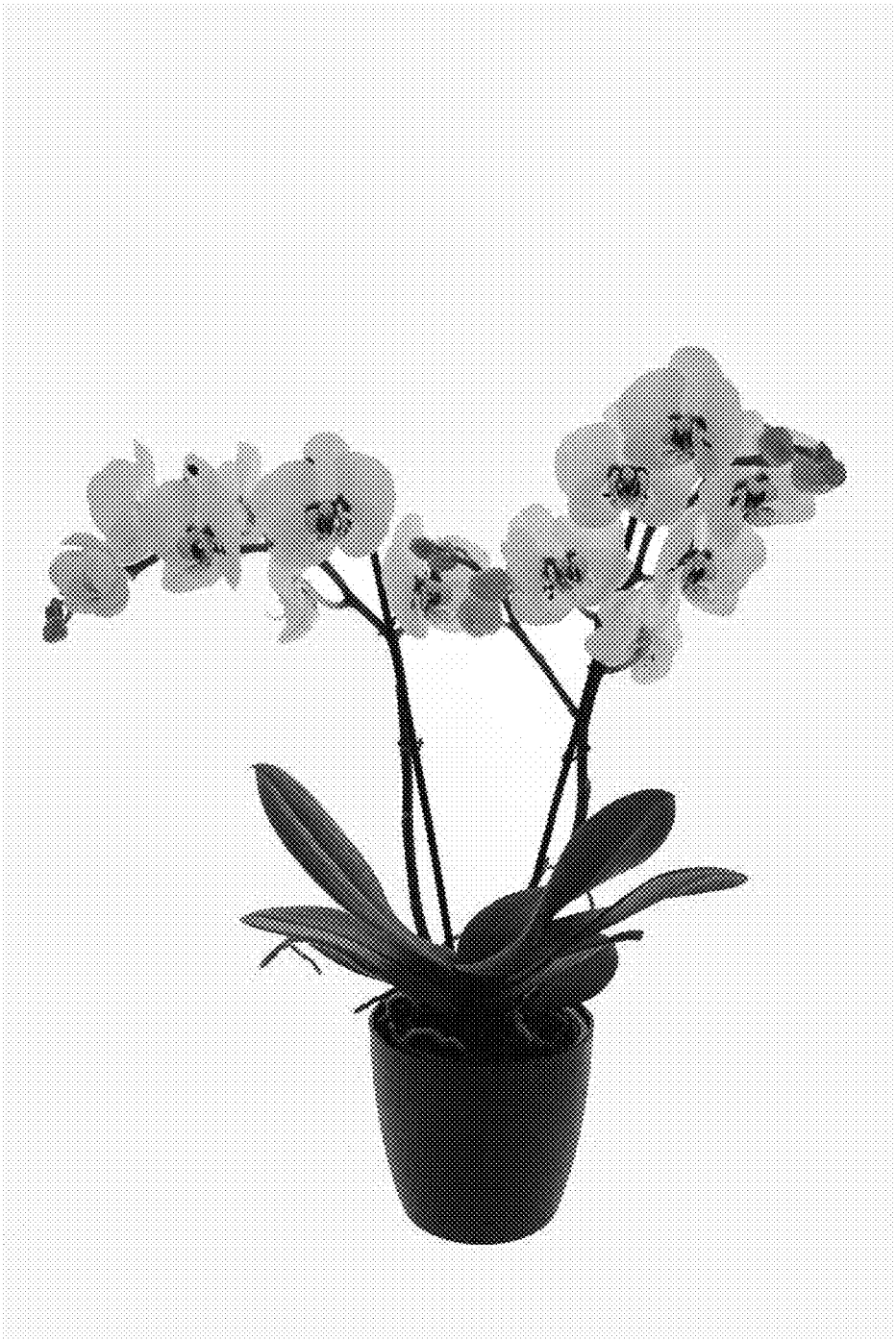

Botanical designation: *Phalaenopsis hybrida.*
Cultivar denomination: 'DIAMOND SKY'.

STATEMENT REGARDING PRIOR DISCLOSURES BY INVENTOR and APPLICANT/ASSIGNEE

An European Community Plant Breeder's Rights application for the instant plant was filed by the Applicant/Assignee of the instant application, Floricultura B. V. of Heemskerk, The Netherlands on Mar. 18, 2021, application number 2021/0828. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Diamond Sky'.

The new *Phalaenopsis* plant is a product of a planned breeding program conducted by the Inventor in Nantou, Taiwan and Heemskerk, The Netherlands. The objective of the breeding program is to develop new fast-growing and freely flowering *Phalaenopsis* plants with good leaf shape and large flowers with unique and attractive patterns and coloration.

The new *Phalaenopsis* plant originated from a cross-pollination on May 27, 2014 in Nantou, Taiwan of *Phalaenopsis hybrida* 'Harck Pearl', not patented, as the female, or seed, parent with *Phalaenopsis hybrida* 'Nankung's 4.55 pm', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in August, 2018.

Asexual reproduction of the new *Phalaenopsis* plant by in vitro meristem propagation in a controlled environment in Assendelft, The Netherlands since August, 2019 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Diamond Sky'. These characteristics in combination distinguish 'Diamond Sky' as a new and distinct *Phalaenopsis* plant:

1. Upright plant habit.
2. Moderately vigorous growth habit.
3. Strong flowering stems.
4. Strong and slightly elongated leaves.
5. Freely flowering habit with typically two inflorescences per plant, each inflorescence with numerous flowers.
6. White-colored flowers with yellow-colored labellum and a small number purple-colored spots surrounding the column.
7. Good postproduction longevity.

Plants of the new *Phalaenopsis* can be compared to plants of the female parent, 'Harck Pearl'. Plants of the new *Phalaenopsis* differ primarily from plants of 'Harck Pearl' in flower color as plants of the new *Phalaenopsis* have white-colored flowers with yellow-colored labellum and a small number purple-colored spots surrounding the column whereas plants of 'Harck Pearl' have white-colored flowers with a large number of purple-colored spots.

Plants of the new *Phalaenopsis* can be compared to plants of the male parent, 'Nankung's 4.55 pm'. Plants of the new *Phalaenopsis* differ primarily from plants of 'Nankung's 4.55 pm' in flower color as plants of the new *Phalaenopsis* have white-colored flowers with yellow-colored labellum and a small number purple-colored spots surrounding the column whereas plants of 'Nankung's 4.55 pm' have white-colored flowers with a larger number of purple-colored spots.

Plants of the new *Phalaenopsis* can be compared to plants of *Phalaenopsis hybrida* 'Big Time', not patented. In side-by-side comparisons, plants of the new *Phalaenopsis* differ primarily from plants of 'Big Time' in flower shape as the curvature of the lateral lobe of the lip of plants of the new *Phalaenopsis* is much less than the curvature of the lateral lobe of the lip of plants of 'Big Time'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Diamond Sky' grown in a container.

Figure 2:
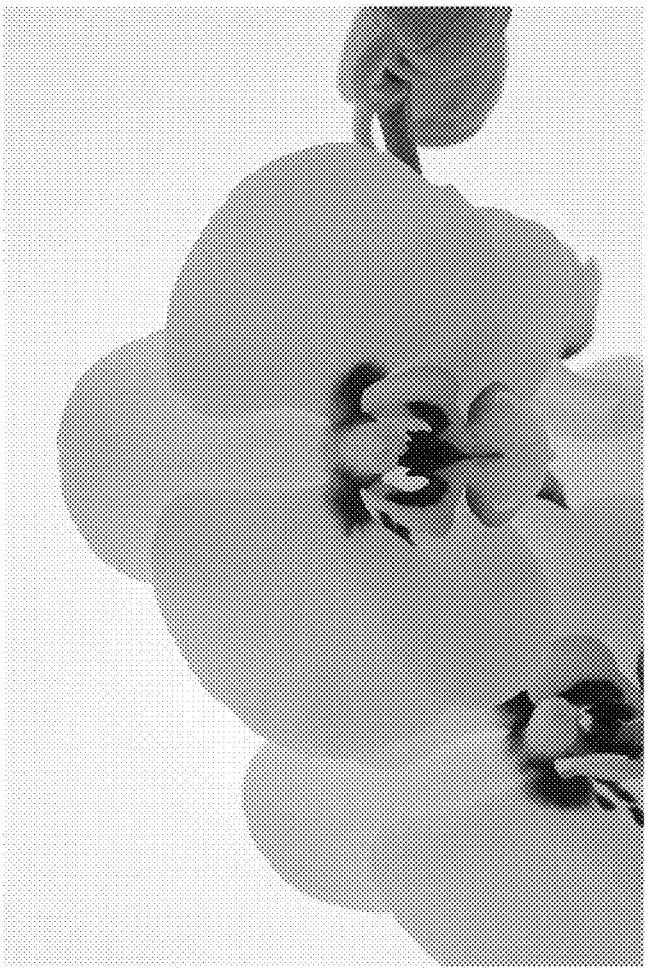

The photograph on the second sheet (FIG. 2) is a close-up view of typical flowers of 'Diamond Sky'.

DETAILED BOTANICAL DESCRIPTION

The aforementioned photographs and following observations and measurements describe plants grown during the late summer and early autumn in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the production of the plants, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Diamond Sky'.

Parentage:

*Female parent.*—*Phalaenopsis hybrida* 'Harck Pearl', not patented.

*Male parent.*—*Phalaenopsis hybrida* 'Nankung's 4.55 pm', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically two inflorescences per plant, each inflorescence with numerous flowers; monopodial; moderately vigorous growth habit and moderate growth rate.

*Plant height, substrate level to top of foliar plane.*—About 14.8 cm.

*Plant height, substrate level to top of inflorescences.*—About 35.8 cm.

*Plant diameter or spread.*—About 38 cm.

Leaf description:

*Arrangement and quantity.*—Distichous, simple; sessile; about six leaves per plant.

*Length.*—About 14.7 cm.

*Width.*—About 7.5 cm.

*Aspect.*—Uptight to slightly outwardly arching.

*Shape.*—Oblong to narrowly obovate; slightly carinate.

*Apex.*—Unequal obtuse.

*Base.*—Sheathing. Sheath length: About 2.3 cm. Sheath width: About 1.3 cm. Sheath color: Close to 144B.

*Margin.*—Entire; not undulate.

*Texture and luster, upper and lower surfaces.*—Smooth, glabrous; slightly glossy.

*Venation pattern.*—Camptodromous.

*Color.*—Developing leaves, upper surface: Close to NN137A. Developing leaves, lower surface: Close to 146B. Fully expanded leaves, upper surface: Close to NN137B; venation, close to NN137A. Fully expanded leaves, lower surface: Close to 146A to 146B; venation, close to 143A.

Inflorescence description:

*Appearance and flowering habit.*—Showy zygomorphic flowers arranged on axillary branched racemes; typically two inflorescences per plant; each inflorescence with about twelve flowers; flowers face outwardly on arching inflorescences supported by upright peduncles; flowers with three petals, two lateral petals and one center petal transformed into a labellum and three sepals.

*Fragrance.*—None detected.

*Time to flower.*—Plants begin flowering about six months after planting; plants flower naturally during the winter into the spring.

*Flower longevity.*—Long flowering period, individual flowers maintain good substance for about seven weeks on the plant; flowers not persistent.

*Inflorescence length* (*lowermost flower to inflorescence apex*).—About 27.6 cm.

*Inflorescence width.*—About 14 cm.

*Flower buds.*—Height: About 1.8 cm. Diameter: About 1.4 cm by 1.5 cm. Shape: Broadly ovate. Color: Close to a blend of 145A and 150A; distally, close to N144D.

*Flower size.*—About 7.8 cm (vertical) by 8.3 cm (horizontal).

*Flower depth.*—About 3.2 cm.

*Petals, quantity and arrangement.*—Three, two lateral petals and one center petal transformed into a labellum.

*Lateral petals.*—Length: About 4 cm. Width: About 5.1 cm. Shape: Reniform; slightly concave. Apex: Obtuse to rounded. Margin: Entire. Texture and luster, upper surface: Smooth, glabrous, moderately velvety; matte. Texture and luster, lower surface: Smooth, glabrous, slightly velvety; matte. Color: When opening, upper surface: Close to NN155C; towards the base, close to 187B and 187C. When opening, lower surface: Close to 155C; towards the margins and apex, close to NN155C; and towards the base, close to N187D. Fully opened, upper surface: Close to NN155D; towards the base, close to N79C and 187C; venation, close to NN155D; color does not change with subsequent development. Fully opened, lower surface: Close to NN155D; towards the base, close to N187D; venation, close to NN155D; color does not change with subsequent development.

*Labella.*—Appearance: Three-parted with two lateral lobes and a central lobe. Length, lateral lobes: About 1.7 cm. Width, lateral lobes: About 1.2 cm. Length, central lobe: About 2.7 cm. Width, central lobe: About 9 mm to 19 mm. Shape, lateral lobes: Obovate. Shape, central lobe: Ovate to roughly deltoid. Apex, lateral lobes: Obtuse. Apex, central lobe: Broadly retuse with two recurved cirrose tips, about 1.5 cm in length and about 1.6 mm in width. Margins, lateral and central lobes: Entire. Texture and luster, upper and lower surfaces: Smooth, glabrous, moderately velvety; matte. Callosities: Located at the base of the labellum and attachment point of the lateral petals; about 4 mm in length, about 6 mm in width and about 5 mm in height. Color: When opening, upper surface: Lateral lobes: Close to NN155D; basal margin, close to 2B; and at the base, close to 187B. Central lobe: Close to 154B and 1B; towards the apex, close to NN155D; apical margin, close to 164A; cirrose tips, close to NN155D; and at the base, close to N186C and 187B to 187C. Callosities: Close to 4C to 4D; distally, close to N186C. When opening, lower surface: Lateral lobes: Close to NN155C; basal margin, close to 2A; and at the base, tinged with close to N187D to lighter than N187D. Central lobe: Close to 157C to 157D; towards the apex, close to NN155C; margins, tinged with close to 154B and 154C; apical margin, close to 164A; cirrose tips, close to NN155C; and at the base, close to lighter than N187D. Fully opened, upper surface: Lateral lobes: Close to NN155D; basal margin, close to 13B; and at the base, close to 187A to 187B. Central lobe: Close to 9B; towards the apex, close to NN155C; apical margin, close to 164B with fine dots, close to 166B; cirrose tips, close to NN155C; and at the base, close to N186C and 187B to 187C. Callosities: Close to 11A; distally, close to a blend of N186C and 200C. Fully opened, lower surface: Lateral lobes: Close to NN155C; basal margin, close to 12B; and at the base, tinged with close to N77C and N77D. Central lobe: Close to 155A; towards the apex, close to NN155C; margins, tinged with close to 7D; apical margin, close to 164A; cirrose tips, close to NN155C; and at the base, close to N187D.

*Sepals.*—Quantity and arrangement: Three, one upper dorsal sepal and two lower lateral sepals. Length, dorsal sepal: About 4.5 cm. Width, dorsal sepal: About 3.8 cm. Length, lateral sepals: About 4.5 cm. Width, lateral sepals: About 3.4 cm. Shape, dorsal sepal: Broadly elliptic. Shape, lateral sepals: Ovate. Apex, dorsal sepal: Obtuse to rounded. Apex, lateral sepals: Obtuse. Base, dorsal and lateral sepals: Truncate. Margin, dorsal and lateral sepals: Entire. Texture and luster, dorsal and lateral sepals, upper and lower surfaces: Smooth, glabrous, moderately velvety; matte. Color, dorsal sepal: When opening, upper surface: Close to 157D; occasionally with one to three large dots, close to 187A and 187B. When opening, lower surface: Close to 150C; towards the margins and apex, close to 157B. Fully opened, upper surface: Close to NN155D; occasionally with one to three large dots, close to 187B and 187C. Fully opened, lower surface: Close to NN155B to NN155C; towards the margins and apex, close to NN155D; occasionally with one to three large dots, close to N79D. Color, lateral sepals: When opening, upper surface: Close to 157A; towards the base, close to 145C with dots, close to 187B and 187C. When opening, lower surface: Close to 150B; towards the margins and apex, close to 150D; towards the base, dots, close to 187C. Fully opened, upper surface: Close to NN155D; towards the base, close to 145D and 157A with dots, close to N186D and 187B. Fully opened, lower surface: Close to 145C and 145D; towards the margins and apex, close to NN155B; towards the base, dots, close to N79D and N187C.

*Peduncles*.—Length: About 44.4 cm. Diameter: About 7 mm. Strength: Strong. Aspect: Upright to outwardly arching. Texture and luster: Smooth, glabrous; matte. Color: Close to 144C; dense fine dots, close to 147A.

*Pedicels*.—Length: About 3.8 cm. Diameter: About 4 mm. Strength: Moderately strong. Aspect: About 60° from peduncle axis. Texture and luster: Smooth, glabrous; matte. Color: Close to 144C; distally, close to 150D.

*Reproductive organs*.—Androecium: Column length: About 9 mm. Column width: About 7 mm. Column color: Close to NN155B. Pollinia quantity: Two. Pollinia diameter (per two pollinia): About 2.25 mm. Pollinia color: Close to 17B. Gynoecium: Stigma length: About 4 mm. Stigma width: About 6 mm. Stigma shape: Reniform. Stigma color: Close to 155C. Ovary length: About 9 mm. Ovary diameter: About 1 mm. Ovary color: Close to 149C to 149D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Diamond Sky' as illustrated and described.

* * * * *